(12) United States Patent
Brassat et al.

(10) Patent No.: US 7,994,345 B2
(45) Date of Patent: Aug. 9, 2011

(54) PROCESS FOR THE PURIFICATION OF THIOPHENES

(75) Inventors: Lutz Brassat, Leverkusen (DE); Stephan Kirchmeyer, Leverkusen (DE)

(73) Assignee: H. C. Starck GmbH (DE)

( * ) Notice: Subject to any disclaimer, the term of this patent is extended or adjusted under 35 U.S.C. 154(b) by 0 days.

(21) Appl. No.: 12/498,739

(22) Filed: Jul. 7, 2009

(65) Prior Publication Data

US 2009/0318710 A1    Dec. 24, 2009

Related U.S. Application Data

(62) Division of application No. 10/942,409, filed on Sep. 16, 2004, now abandoned.

(30) Foreign Application Priority Data

Sep. 23, 2003  (DE) .................. 103 43 873

(51) Int. Cl.
  *C07D 495/04* (2006.01)
  *C07D 333/02* (2006.01)
(52) U.S. Cl. .......................................... 549/50; 549/29
(58) Field of Classification Search .................. 549/50, 549/29
  See application file for complete search history.

(56) References Cited

U.S. PATENT DOCUMENTS

| | | | |
|---|---|---|---|
| 4,959,430 A | 9/1990 | Jonas et al. | |
| 4,987,042 A | 1/1991 | Jonas et al. | |
| 5,035,926 A | 7/1991 | Jonas et al. | |
| 6,077,961 A | 6/2000 | Labat et al. | |
| 6,369,239 B2 | 4/2002 | Rauchschwalbe et al. | |
| 6,825,357 B2 | 11/2004 | Rauchschwalbe et al. | |
| 7,094,865 B2 | 8/2006 | Groenendaal et al. | |
| 7,202,369 B2 | 4/2007 | Baik et al. | |
| 2001/0034453 A1 | 10/2001 | Rauchschwalbe et al. | |
| 2003/0028024 A1* | 2/2003 | Rauchschwalbe et al. | ... 544/345 |
| 2003/0055130 A1 | 3/2003 | Groenendaal et al. | |

FOREIGN PATENT DOCUMENTS

| | | |
|---|---|---|
| JP | 11-269168 A | 10/1999 |
| WO | WO-02/079295 A1 | 10/2002 |
| WO | WO-03/054053 A1 | 7/2003 |

OTHER PUBLICATIONS

Ulrich and Neumann, Journal of Thermal Analysis 1997, 48, 527-533.*
JW Mullin, Chapter 8 in Crystallization 2001, 4th Ed. Butterworth Heinemann (Pub.).*
Bauerle et al. Chem. Commun. 2002, 2690-2691.
Chemical Engineering, 93(8), Apr. 28, 1986, Nicholas Wynn, pp. 26-27, "Use Melt Crystalization for Higher Purities".
Handbook of Industrial Chrystallization, 2nd ed., (month unavailable) 2000, pp. 161-179, J. Ulrich and H.C. Buelau, "Melt Crystallization".
Sigma Aldrich Chemical Catalog, 2001-2002; p. 607.
Welsh et al. (Advanced Materials 1999, 11(16), 1379-1382.
Zong et al. (Chem. Commun. 2002, 2498-99).
Coffey, et al., "A Facile Synthesis of 3,4-Dialkoxythiophenes," *Synthetic Communications* (1996), vol. 26, No. 11, pp. 2205-2212.
"A chemical experiment manual," (1963), the first volume, pp. 371-399.
Japanese Office Action dated Sep. 14, 2010.

* cited by examiner

*Primary Examiner* — Jason M Nolan
(74) *Attorney, Agent, or Firm* — Connolly Bove Lodge & Hutz LLP

(57) ABSTRACT

The invention relates to a process for the purification of thiophenes by means of precipitation. The purified thiophenes are liquid at room temperature, have a purity of at least 99.50 wt. %, and are represented by the following general formula (I),

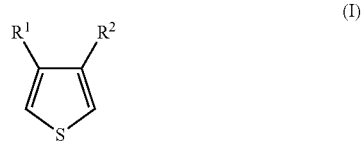

(I)

wherein $R^1$ and $R^2$ independently of each other are, for example, a linear or branched $C_1$-$C_{20}$-alkyl group, or together form a fused $C_1$-$C_{20}$-dioxyalylene ring. The process involves: (I) precipitating the thiophene by cooling a solution of the thiophene and at least one solvent; or (II) precipitating the thiophene by adding the thiophene to a cooled solution of solvent and optionally the thiophene. The solutions are cooled to a temperature below the melting point of the thiophene.

18 Claims, No Drawings

PROCESS FOR THE PURIFICATION OF THIOPHENES

CROSS REFERENCE TO RELATED PATENT APPLICATION

This application is a divisional of U.S. patent application Ser. No. 10/942,409, filed Sep. 16, 2004, which claims the right of priority under 35 U.S.C. §119(a)-(d) of German Patent Application No. DE 103 43 873.4, filed Sep. 23, 2003.

FIELD OF THE INVENTION

The invention relates to a process for the purification of thiophenes which are liquid at room temperature, the thiophenes purified by this process and their use.

BACKGROUND OF THE INVENTION

Thiophenes are used, for example, for the preparation of conductive polymers. Poly(3,4-alkylenedioxythiophenes) such as are described, for example, in EP-A 339 340, are of particular interest in this context. These compounds are distinguished by particular properties, such as high conductivity, high transparency and outstanding long-term stability. They have therefore found increasing use in industry as organic conductive polymers. Thus e.g. through-plating of printed circuit boards, antistatic treatment of photographic films and use as an electrode or solid electrolyte in solid electrolyte capacitors are described as important fields of use.

An important prerequisite in the preparation of organic conductive polymers is high purity of the starting substances needed for their preparation. Impurities contained in the starting substance can adversely influence the polymerization in that the polymerization does not take place, or takes place only very slowly or incompletely, or is accelerated to an uncontrolled extent. The processing time of these monomers can consequently drop drastically, so that these can no longer be employed in the processing processes.

In addition, the properties of the resulting polymers may also be adversely influenced in that the impurities, for example, adversely change the intrinsic colour of the resulting polymer and as a result the transparency, which is essential for the use of the polymers e.g. as transparent conductive or antistatic coatings, is impaired.

Impurities which are also capable of polymerization can be co-incorporated into the polymer and thereby significantly lower the conductivity thereof. Further adverse effects of impurities can be that the order of the conductive layers may be lowered by impurities, whereby poorer conductivities result, that impurities become concentrated on the surface of the polymer after the polymerization and undesirable transition resistances thereby result, so that the function of the conductive layer is restricted, or that the long-term stability of the conductive polymers is adversely influenced in that the impurities, for example, initiate reaction of the conductive polymer with oxygen and thus significantly impair the properties of the polymer.

The starting substances which are needed for the preparation of organic conductive polymers and are as a rule prepared from raw materials by chemical reactions, are therefore purified before their use.

A number of purification operations which are in principle suitable for purification of the monomers for the polymerization to give organic conductive polymers are known to the expert. Such purification methods are, for example, distillation, sublimation, extraction, crystallization, chromatography and adsorption. These purification methods have been known to the expert for a long time and are described in the usual textbooks.

Thiophenes which are liquid at room temperature and are suitable for the preparation of electrically conductive polymers are of particular importance because of their easy processability in the liquid form. For the purification of these thiophenes the expert has available the purification methods which can be used on liquid substances, preferably distillation, which is also carried out on a large industrial scale, extraction and chromatography.

Distillative purification of thiophenes as monomers for use for the preparation of electrically conductive polymers is known, for example, from EP-A 1 142 888. The doctrine of EP-A 1 142 888 is that the number and amount of by-products can be reduced by optimized reaction conditions and e.g. 3,4-ethylenedioxythiophene is obtainable in a purity of up to 97.7%. However, the doctrine of EP-A 1 142 888 furthermore is that for further purification an additional extraction is necessary in order to remove water-soluble by-products and to achieve a purity of more than 99%. 3,4-Dimethoxythiophene predominantly occurs as a secondary component, i.e. impurity, in this synthesis of 3,4-ethyleniedioxythiophene.

Furthermore, separating off of compounds by distillation is only possible if the components to be separated differ significantly, i.e. by more than 1° C., in their boiling points. The less the boiling points differ, the greater the expenditure on apparatus for the separation, so that such separations are no longer to be carried out economically. Since substituted thiophenes, such as, for example, alkylenedioxythiophenes, are preferably distilled under reduced pressure, the difference in the boiling points is reduced further, which further increases the expenditure on separation.

The purification of 3,4-allylenedioxythiophenes, in particular of 3,4-ethylenedioxythiophene, which are contaminated with 3,4-dimethoxythiophene represents a particular difficulty. Thus, for example, 3,4-dimethoxythiophene produced during the synthesis of 3,4-ethylenedioxythiophene can be separated off only with a high expenditure because of the molecular weight differing by only two units and the very similar structure, which makes purification via distillation no longer economical beyond a certain degree of purity. 3,4-Dimethoxythiophene as an impurity has the disadvantage, however, that it is co-incorporated into the polymer during polymerization and can thus adversely influence properties of the polymer, such as, for example, the conductivity.

Chromatographic purification of thiophenes as monomers for use for the preparation of electrically conductive polymers is also known. WO-A 02/79295 describes the preparation of liquid and solid chiral alkylenedioxythiophenes and mentions in examples the purification by chromatography on silicon dioxide. The compounds prepared according to WO-A 02/79295 have purities of up to 99.7% after purification. However, chromatographic separation also has disadvantages. Thus, large amount of solvents are needed to carry it out, since the compounds to be separated must be in a very dilute form in order to achieve the desired separation effect. Furthermore, the chromatographic separation cannot be operated continuously with the aid of simple apparatuses, so that in each case only small amounts of the desired purified thiophene are obtained. A continuous separation of large amounts would therefore be associated with an extremely high expenditure on apparatus, so that such a purification of thiophenes can no longer be carried out economically.

Conventional recrystallization in which thiophenes which are solid at room temperature are dissolved at elevated temperature, usually under reflux of the solvent, and are then crystallized out again by cooling is also known for the purification of thiophenes as monomers for use for the preparation of electrically conductive polymers and is described in WO-A 02/79295, but is limited to thiophenes which are solid at room tm.

A particular form of crystallization can also be used for the crystallization of liquid thiophenes. This specific form of crystallization, melt crystallization, is described, for example, in N. Wynn, Chem. Engineering (1986), 93(8), 26-27 and in J. Ulrich and H. C. Bülau, Editor(s): Myerson, Allan S. "Handbook of Industrial Crystallization (2nd Edition)" (2002), 161-179. Melt crystallization is substantially based on cooling a liquid substance until a melt is formed, from which only the substance to be purified crystallizes out. After crystallization, the mother liquid, which in the ideal case contains all the impurities, is separated off. Where appropriate, the crystallized substance is heated gently so that impurities adhering to the product can be removed together with some of the substance which is then melting. However, this process is limited to substances or substance mixtures which contain relatively large amounts of impurities which can be separated off in liquid form. Small amounts of impurities can be removed only uneconomically via this process, since large amounts of the desired compound have to be separated off at the same time in order to wash out the small amount of impurity. Moreover, melt crystallization is critical in respect of the temperature programme and therefore expensive on apparatus.

SUMMARY OF THE INVENTION

There was therefore still a need for a process for the purification of thiophenes which are liquid at room temperature in which an extremely high purity, preferably of more than 99.9%, is achieved and which does not have the disadvantages described above.

The present invention was therefore based on the object of discovering a less expensive process for the purification of thiophenes with which highly pure 3,4-allylenedioxythiophenes, preferably with a purity of more than 99.9%, can be prepared.

In accordance with the present invention, there is provided a process for purifying a thiophene represented by general formula (I),

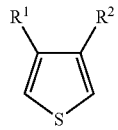

(I)

wherein,
$R^1$ and $R^2$ are each selected independently from the group consisting of hydrogen,
linear or branched, optionally substituted $C_1$-$C_{20}$-alkyl groups, linear or branched $C_1$-$C_{20}$-oxyalkyl groups, linear or branched $C_1$-$C_{20}$-oxyalkyl groups which are interrupted by 1 to 5 oxygen atoms, linear or branched $C_1$-$C_{20}$-oxyalkyl groups which are interrupted by 1 to 5 sulphur atoms, a fused ring of linear or branched, optionally substituted $C_1$-$C_{20}$-dioxyalkylene formed by $R^1$ and $R^2$ together, and a fused ring of linear or branched, optionally substituted $C_1$-$C_{20}$-dioxyarylene formed by $R^1$ and $R^2$ together, and
said thiophene being liquid at room temperature,
said method being selected from the group consisting of,
a method (I) comprising, (a) providing a first solution comprising said thiophene and at least one solvent, and
(b) cooling said first solution to a temperature below the melting temperature of said thiophene, thereby precipitating said thiophene as a solid from said first solution, and
a method (II) comprising, (a) providing a second solution comprising at least one solvent and optionally said thiophene,
(b) cooling said second solution to a temperature below the melting temperature of said thiophene, to form a cooled second solution, and
(c) adding said thiophene to said cooled second solution, thereby precipitating said thiophene as a solid from said cooled second solution.

Unless otherwise indicated, all numbers or expressions, such as those expressing process conditions, etc., used in the specification and claims are understood as modified in all instances by the term "about."

DETAILED DESCRIPTION OF THE INVENTION

In the context of the invention, thiophenes which are liquid at room temperature are to be understood as those thiophenes which have their melting point below +40° C., preferably below +30° C.

In the context of the invention, room temperature can be a temperature of 10 to 40° C., preferably 15 to 30° C., particularly preferably 18 to 25° C.

Thiophenes of the general formula (I) which are preferably purified with the process according to the invention are compounds of the general formula (II)

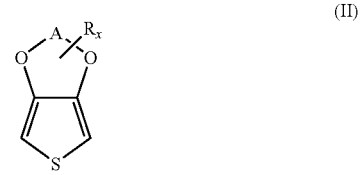

(II)

wherein

A represents an optionally substituted $C_1$-$C_5$-allylene radical or a $C_1$-$C_{12}$-arylene radical, preferably an optionally substituted $C_2$-$C_3$-allylene radical, R represents a linear or branched, optionally substituted $C_1$-$C_{18}$alkyl radical, preferably linear or branched, optionally substituted $C_1$-$C_{14}$-allyl radical, an optionally substituted $C_5$-$C_{12}$-cycloalkyl radical, an optionally substituted $C_6$-$C_{14}$-aryl radical, an optionally substituted $C_7$-$C_{18}$-aralkyl radical, an optionally substituted $C_1$-$C_4$-hydroxyallyl radical, preferably optionally substituted $C_1$-$C_2$-hydroxyallyl radical, or a hydroxyl radical, x represents an integer from 0 to 8, preferably from 0 to 6, particularly preferably 0 or 1 and in the case where several radicals R are bonded to A, these can be identical or different.

The general formula (II) is to be understood such that the substituent R can be bonded to the allylene or arylene radical A x times.

Preferred compounds of the general formula (II) are those of the general formula (IIa)

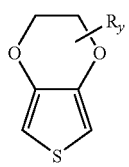

wherein
R has the meaning given in the general formula (II) and y represents 0, 1, 2, 3 or 4.

In the context of the invention, $C_1$-$C_5$-alkylene radicals A are methylene, ethylene, n-propylene, n-butylene or n-pentylene. In the context of the invention, $C_1$-$C_{12}$-arylene radicals can be, for example, phenylene, naphthylene, benzylidene or anthracenylidene. In the context of the invention, $C_1$-$C_{18}$- represents linear or branched $C_1$-$C_{18}$-alkyl radicals, such as, for example, methyl, ethyl, n- or iso-propyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl or n-octadecyl. $C_1$-$C_{20}$-alkyl groups moreover include, for example, n-nonadecyl and n-eicosyl. In the context of the invention, $C_5$-$C_{12}$-cycloalkyl represents $C_5$-$C_{12}$-cycloalkyl radicals, such as, for example, cyclopentyl, cyclohexyl, cycloheptyl, cyclooctyl, cyclononyl or cyclodecyl, $C_5$-$C_{14}$-aryl represents $C_5$-$C_{14}$-aryl radicals, such as, for example, phenyl or naphthyl, and $C_7$-$C_{18}$-aralkyl represents $C_7$-$C_{18}$-aralkyl radicals, such as, for example, benzyl, o-, m- or p-tolyl, 2,3-, 2,4-, 2,5-, 2,6-, 3,4- or 3,5-xylyl or mesityl. In the context of the invention, $C_1$-$C_{20}$-oxyalkyl represents $C_1$-$C_{20}$-oxyalkyl radicals, such as, for example, methoxy, ethoxy, n- or iso-propoxy, n-, iso-, sec- or tert-butoxy, n-pentyloxy, 1-methylbutyloxy, 2-methylbutyloxy, 3-methylbutyloxy, 1-ethylpropyloxy, 1,1-dimethylpropyloxy, 1,2-dimethylpropyloxy, 2,2-dimethylpropyloxy, n-hexyloxy, n-heptyloxy, n-octyloxy, 2-ethylhexyloxy, n-nonyloxy, n-decyloxy, n-undecyloxy, n-dodecyloxy, n-tridecyloxy, n-tetradecyloxy, n-hexadecyloxy, n-octadecyloxy, n-nonadecyloxy or n-eicosyloxy. The preceding list serves to explain the invention by way of example and is not to be regarded as conclusive. Further substituents of the alkylene or arylene radicals A which are optionally possible are numerous organic groups, for example alkyl cycloalkyl, aryl halogen, ether, thioether, disulfide, sulfoxide sulfone, sulfonate, amino, aldehyde, keto, carboxylic acid ester, carboxylic acid, carbonate, carboxylate, cyano, alkylsilane and alkoxysilane groups, as well as carboxylamide groups.

If the thiophene to be purified has one or more stereocentres, the thiophene can be a racemate, an enantiomerically pure or diastereomerically pure compound or an eniantiomerically enriched or diastereomerically enriched compound. An enantiomerically enriched compound is to be understood as meaning a compound having an entantiomer excess (ee) of more than 50%. A diastereomerically enriched compound is to be understood as meaning a compound having a diastereomer excess (de) of more than 30%. According to the invention, however, the compound can also be any desired mixture of diastereomers.

Before purification with the process according to the invention, the thiophene to be purified preferably has a purity of greater than 70%, particularly preferably a purity of greater than 90%.

The thiophenes of the general formulae (I), (II) or (IIa) to be purified can be prepared by processes known to the expert. Such a preparation process is described, for example, in EP-A 1 142 888.

Solvents which are employed are those in which the thiophene to be purified dissolves and which have a sufficiently low melting point, preferably below -40° C. Examples of suitable solvents which may be mentioned are isobutyl methyl ketone, chloroform, methylene chloride, toluene, methanol, propanol, ethanol, acetone, iso-propanol, n-butanol, sec-butanol, dimethylformamide, methyl tert-butyl ether, tetrahydrofuran, diethyl ether, hexane or pentane.

Preferred solvents are polar solvents, and alcohols are particularly preferred in this context. Methanol or ethanol are very particularly preferred.

The solvent can also be a mixture of two or more solvents.

Mixtures of one or more alcohol(s) optionally with one or more farther solvent(s) are preferred in this context. For this purpose it is not absolutely necessary for each individual solvent to dissolve the thiophene and to have a correspondingly low melting point, merely the mixture must have these properties. A mixture of two alcohols is particularly preferred, and a mixture of methanol and ethanol is very particularly preferred.

The solvent is mixed with the thiophene in a ratio of 0.01:1 to 10:1, preferably in a ratio of 0.3:1 to 3:1 and very particularly preferably in a ratio of 1:1.

The new process is carried out e.g. by a procedure in which the thiophenes to be purified and at least one solvent are brought together in any desired sequence, the solvent or solvents, before being brought together with the thiophene, or the solution obtained during or after bringing them together, is or are cooled down to a temperature at which a mixture of a solid and a liquid forms, the mixture of a solid and a liquid is optionally subsequently stirred and the solid is then separated off.

Preferably, the solvent or solvents before being brought together with the thiophenes, or the solution obtained during or after bringing them together is or are cooled down to a temperature which is at least 10° C., preferably at least 20° C. below the melting temperature of the pure thiophene to be purified. Cooling particularly preferably takes place to 0° C. or lower, very particularly preferably to −15° C. or lower.

The new process can be carried out, for example, by dissolving the thiophenes in the solvent(s) and then cooling this solution down at least to the extent that the purified thiophene precipitates out or crystallizes out.

In this procedure, the thiophene call be dissolved in the solvent(s) at a temperature above the melting point of the thiophene. In this context a temperature of between 0° C. and +40° C. is preferred. A temperature of between +15° C. and +25° C. is particularly preferred.

The solution obtained from the solvent and the thiophene is then cooled. The solution is cooled here until the thiophene separates out or crystallizes out of the solution in the form of a solid. Preferably, the solution is cooled to a temperature of at least 20° C. below the melting temperature of the pure thiophene. Cooling to −15° C. or to a temperature of lower than −15° C. is particularly preferred.

The solution is preferably cooled down at a rate such that the thiophene crystallizes out within a period of a few minutes to several hours. Cooling down to the desired temperature over a period of approx. one hour is preferred here.

The cooling down can be effected by external cooling or by introduction of an inert cooling medium. The cooling down is preferably achieved by external cooling.

During the cooling phase, the thiophene separates out of the solution as a solid, for example in the form of crystals. In this context, the solid obtained call contain the thiophene as the pure substance or can consist of a mixture of the solvent(s) and the thiophene.

Alternatively, the new process can be carried out by a procedure in which the liquid thiophene is metered into the already cooled solvent. Solvent mixture or cooled thiophene solution.

In this case the solvent is cooled to a temperature of at least 20° C. below the melting temperature of the pure thiophene. Cooling to −15° C. or a temperature of lower than −15° C. is particularly preferred.

The liquid thiophene is then metered into the cooled solvent—preferably over a period of a few minutes to several hours. The metering rate is to be chosen here such that the thiophene does not precipitate out or crystallize out too rapidly and impurities are thereby also included in the solid. A metering time of at least 1 hour is preferred. However, metering times of less than one hour may also be sufficient, depending on the amount of thiophene which must be metered in. The solid obtained can also contain the thiophene as the pure substance or consist of a mixture of the solvent(s) and the thiophene.

Preferably, the suspension obtained is then subsequently stirred for a period of 1 minute up to 5 hours. A subsequent stirring time of approx. three hours is particularly preferred here.

The subsequent stirring is carried out at a temperature of at least 20° C. below the melting temperature of the pure thiophene. A temperature of −15° C. or a temperature of lower than −15° C. is preferred here.

The product which has precipitated out or crystallized out is then separated off by known methods. This separating off is preferably carried out by a filtration. The filtration can be carried out under normal pressure or under pressure.

The filtration is preferably carried out with the aid of a filter unit which can be temperature-controlled, and is preferably carried out such that the product to be filtered is present as a solid during the filtration. The filtration is preferably carried out at a temperature of between 0° C. and −20° C. Preferably, the filtration is carried out at −15° C. or a temperature of lower than −15° C.

Thereafter, the solid obtained can be washed with one or more solvent(s) in order to remove residues of impurities from the filter cake. Polar solvents are preferably used for this purpose. Alcohols, optionally in a mixture with one another and/or with further solvents, are particularly preferably used. The solid is particularly preferably washed with ethanol or methanol or a mixture of these.

In the case where the filter cake is washed to remove impurities adhering to the filter cake, it is appropriate to cool the washing agent, i.e. the solvent used for the washing, in order to prevent relatively large amounts of purified thiophene from dissolving in the washing agent. The washing agent has a temperature below 0° C. during the washing. Preferably, the washing agent is cooled down to −15° C. or lower for the washing.

The solid then obtained is warmed to a temperature above the melting point of the thiophene over a period of between 5 minutes and 5 hours. Preferably, the solid is allowed to melt over a period of 1 hour.

After the melting, the molten solid may still contain residues of the solvent added before the crystallization or residues of the washing agent. These residues can be removed by methods known to the expert, e.g. by simple distillation. The solvent is distilled over during the distillation. The distillation can be carried out under normal pressure or under reduced pressure. Preferably, it is carried out under reduced pressure at temperatures of between 30° C. and 150° C., preferably between 50° C. and 100° C.

The thiophene obtained in this way, which remains as the bottom product, preferably has a purity of at least 99.50%, preferably at least 99.9%, after the solvent has been distilled off completely. For example, thiophenes which have been synthesized using 3,4-dimethoxythiophene or during the synthesis of which 3,4-dimethoxythiophene is produced as a by-product contain less than 0.05 wt. % of 3,4-dimethoxythiophene after purification with the process according to the invention. Such a low content of 3,4-dimethoxythiophene cannot be achieved or can be achieved only with a very high loss in the yield of the desired thiophene with conventional purification processes, such as e.g. simple distillation.

Thiophenes of such purity are not known. Therefore another subject matter of the invention is a thiophene of the general formula (I),

wherein
R$^1$ and R$^2$ independently of one another represent hydrogen, optionally substituted C$_1$-C$_{20}$-allyl groups or C$_1$-C$_{20}$-oxyalkyl groups which are optionally interrupted by 1 to 5 oxygen and/or sulfur atoms, or together represent an optionally substituted C$_1$-C$_{20}$-dioxyalkylene or C$_1$-C$_{20}$-dioxyarylene group,
characterized in that it has a purity of at least 99.50 wt. %, in particular of the least 99.9 wt. %.

Particular preferred is a 3,4-ethylene-dioxythiophene with such purity.

Unless mentioned otherwise—all the purity data are data in percent by weight.

The thiophene remaining as the bottom product after the distillation call also be distilled over to separate off traces of colouring substances. As a rule, a thiophene which is colourless to the eye is obtained by this means. The distillation of the thiophene is also preferably carried out under reduced pressure.

By way of example, up to 70%, preferably up to 90%, particularly preferably up to 95% and very particularly preferably virtually 100% of the thiophene employed is obtained in the purified form, depending on the amount of solvent used in relation to the amount of thiophene employed and depending on the temperature during the precipitation and, where appropriate, during the washing. Any remaining portion of the thiophene employed remains dissolved in the mother liquor, i.e. e.g. in the filtrate separated off during the filtration, or, where appropriate, in the washing agent. Since a recovery, in the purified form, of virtually 100% of the thiophene employed is desirable, in a preferred embodiment the purification process can also be carried out by a procedure in which the mother liquor of a preceding precipitation or crystallization and/or the washing agent is or are employed again as solvent or together with the solvent in the process for the purification of further thiophene.

The process according to the invention renders possible the purification of thiophenes in a simple procedure. The products are moreover obtained in good yields.

Because of their high purity, the thiophenes purified by the process according to the invention are outstandingly suitable for the preparation of conductive polymers or for the preparation of organic semiconductors which are suitable e.g. in the production of capacitors, printed circuit boards, antistatic layers, transparent conductive layers, displays, electrochromic glazing and integrated semiconductor circuits. These uses are further subject matter of the invention.

The following compounds may be mentioned by way of example as compounds which can be purified with the process according to the invention: 3,4-ethylenedioxythiophene, 3,4-methylenedioxythiophene; R,S-3,4-(1'-hydroxymethyl) ethylenedioxythiophene, S-3,4-(1'-hydroxymethyl)ethyleniedioxythiophene; R-3,4-(1'-hydroxymethyl)ethylenedioxythiophene, 3,4-(2'-hydroxy)propylenedioxythiophene; 3,4-(1'-methyl)ethylenedioxythiophene, 3,4-(3'-tert-butyl) benzodioxythiophene; 3,4-(1'-n-hexyl)ethylenedioxythiophene; 3,4-(1'-ethyl)ethylenedioxythiophene; 3,4-(1'-n-propyl)ethylenedioxythiophene; 3,4-(1'-butyl) ethylenedioxythiophene; thieno[3,4-b]-1,4-oxathiine; 3,4-ethylenedioxythiophene-1-methyl N-methylcarbamate; 3,4-ethylenedioxythiophene-1-methyl N-ethylcarbamate; 3,4-ethylenedioxythiophene-1-methyl N-hexylcarbamate; 3,4-ethylenedioxythiophene-1-methyl N-phenylcarbamate; 3,4-ethylenedioxythiophene-1-methyl N-tolylcarbamate; (3,4-ethylenedioxythiophene-1-methyl)methyl ether; (3,4-ethylenedioxythiophene-1-methyl)ethyl ether; (3,4-ethyleniediooxythiophene-1-methyl) propyl ether; (3,4-ethylenedioxythiophene-1-methyl) hexyl ether; 3-hexylthiophene; and 3-octylthiophene.

EXAMPLES

Example 1

Purification of 3,4-ethylenedioxythiophene 1,800 g 3,4-ethylenedioxythiophene having a purity of 98.4% and a content of 3,4-dimethoxythiophene of 0.3% and a slightly yellowish colour were stirred with 2,400 ml ethanol in a sulfonating beaker. The solution was cooled down to a temperature of −15° C. by external cooling and stirred at −15° C. for 3 h. The solid formed was separated off with the aid of a suction filter and washed with ethanol precooled to −15° C. The filter cake was warmed to a temperature of +20° C. In a distillation apparatus comprising a reservoir flask, a distillation bridge and a condensation flask, the solvent was first distilled off under a pressure of 16 hPa at a temperature of 50° C. and 3,4-ethylenedioxythiophene was then distilled at a temperature of 90° C. under a pressure of 16 hPa. 1,374 g 3,4-ethylene-dioxythiophene (76% of theory) were obtained in a purity of 100%. The colourless product no longer contained 3,4-dimethoxythiophene.

Example 2

Purification of 3,4-ethylenedioxythiophene 1,800 g 3,4-ethylenedioxythiophene having a purity of 70% and a content of 3,4-dimethoxythiophene of 0.3% and a dark brown colour were stirred with 1,800 ml ethanol in a sulfonating beaker. The solution was cooled down to a temperature of −23° C. by external cooling and stirred at −23° C. for 3 h. The solid formed was separated off with the aid of a suction filter and washed with ethanol precooled to −15° C. The filter cake separated off was warmed to a temperature of +20° C. In a distillation apparatus comprising a reservoir flask, a distillation bridge and a condensation flask, the solvent was first distilled off under a pressure of 12 hPa at a temperature of 50° C. and 3,4-ethylenedioxythiophene was then distilled at a temperature of 90° C. under a pressure of 12 hPa. 718 g 3,4-ethyleniedioxythiophene (55% of theory) were obtained in a purity of 99.2%. The product no longer contained 3,4-dimethoxythiophene.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for purifying a thiophene represented by general formula (I),

wherein,
R$^1$ and R$^2$ are each selected independently from the group consisting of hydrogen, linear or branched C$_1$-C$_{20}$-alkyl groups, linear or branched C$_1$-C$_{20}$-oxyalkyl groups, linear or branched C$_1$-C$_{20}$-alkyl groups which are interrupted by 1 to 5 oxygen atoms, linear or branched C$_1$-C$_{20}$-oxyalkyl groups which are interrupted by 1 to 5 sulphur atoms, a fused ring of linear or branched C$_1$-C$_{20}$-dioxyalkylene formed by R$^1$ and R$^2$ together, and a fused ring of linear or branched C$_1$-C$_{20}$-dioxyarylene formed by R$^1$ and R$^2$ together, and
said thiophene being liquid at room temperature,
said method being selected from the group consisting of,
a method (I) comprising,
  (a) providing a first solution comprising said thiophene and at least one solvent, and
  (b) cooling said first solution to a temperature below the melting temperature of said thiophene, thereby precipitating said thiophene as a solid from said first solution, and
a method (II) comprising,
  (a) providing a second solution comprising at least one solvent and optionally said thiophene,
  (b) cooling said second solution to a temperature below the melting temperature of said thiophene, to form a cooled second solution, and
  (c) adding said thiophene to said cooled second solution, thereby precipitating said thiophene as a solid from said cooled second solution.

2. The process of claim 1 wherein said thiophene is a compound represented by general formula (II)

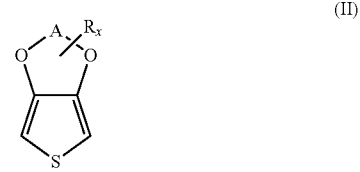

wherein

A is selected from the group consisting of a $C_1$-$C_5$-alkylene radical, a substituted $C_1$-$C_5$-alkylene radical, a $C_1$-$C_{12}$-arylene radical and a substituted $C_1$-$C_{12}$arylene radical, the substituted groups of said substituted $C_1$-$C_5$-alkylene radical and said substituted $C_1$-$C_{12}$-arylene radical being selected independently from the group consisting of halogen, ether, thioether, disulfide, sulfoxide, sulfone, sulfonate, amino, aldehyde, keto, carboxylic acid ester, carboxylic acid, carbonate, carboxylate, cyano, alkylsilane, alkoxysilane and carboxylamide groups, R is selected, independently for each x, from the group consisting of a linear or branched $C_1$-$C_{18}$-alkyl radical, a $C_5$-$C_{12}$-cycloalkyl radical, a $C_6$-$C_{14}$-aryl radical, a $C_7C_{18}$-aralkyl radical, a $C_1$-$C_4$-hydroxyalkyl radical and a hydroxyl radical, x represents an integer from 0 to 8.

3. The process of claim 2 wherein said thiophene is a compound represented by the general formula (IIa),

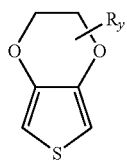

(IIa)

wherein

A is, independently for each y, as defined in claim 2, and y denotes 0, 1, 2, 3 or 4.

4. The process of claim 3 wherein y is 0 or 1.

5. The process of claim 1 wherein said solvent comprises at least one alcohol.

6. The process of claim 1 wherein the said first solution and said second solution are each cooled to a temperature that is at least 20° C. below the melting point of said thiophene.

7. The process of claim 1 wherein said method (I) further comprises separating the precipitated solid thiophene from said first solution at a temperature that is at least 20° C. below the melting point of said thiophene, and said method (II) further comprises separating the precipitated solid thiophene from said cooled second solution at a temperature that is at least 20° C. below the melting point of said thiophene.

8. The process of claim 1 wherein said method (I) further comprises removing residual solvent from the precipitated solid thiophene by means of distillation, and said method (II) further comprises removing residual solvent from the precipitated solid thiophene by means of distillation.

9. A process for purifying a 3,4-ethylenedioxy thiophene, and said thiophene being liquid at room temperature, said method being selected from the group consisting of, a method (I) comprising, (a) providing a first solution comprising said thiophene and at least one solvent, and (b) cooling said first solution to a temperature below the melting temperature of said thiophene, thereby precipitating said thiophene as a solid from said first solution, and a method (II) comprising, (a) providing a second solution comprising at least one solvent and optionally said thiophene, (b) cooling said second solution to a temperature below the melting temperature of said thiophene, to form a cooled second solution, and (c) adding said thiophene to said cooled second solution, thereby precipitating said thiophene as a solid from said cooled second solution and said thiophene is 3,4-ethylenedioxy thiophene.

10. The process of claim 9 wherein said solvent comprises at least one alcohol.

11. The process of claim 9 wherein the said first solution and said second solution are each cooled to a temperature that is at least 20° C. below the melting point of said thiophene.

12. The process of claim 9 wherein said method (I) further comprises separating the precipitated solid thiophene from said first solution at a temperature that is at least 20° C. below the melting point of said thiophene, and said method (II) further comprises separating the precipitated solid thiophene from said cooled second solution at a temperature that is at least 20° C. below the melting point of said thiophene.

13. The process of claim 9 wherein said method (I) further comprises removing residual solvent from the precipitated solid thiophene by means of distillation, and said method (II) further comprises removing residual solvent from the precipitated solid thiophene by means of distillation.

14. The process of claim 4, wherein said solvent comprises at least one alcohol.

15. The process of claim 14, wherein the said first solution and said second solution are each cooled to a temperature that is at least 20° C. below the melting point of said thiophene.

16. The process of claim 15, wherein said method (I) further comprises separating the precipitated solid thiophene from said first solution at a temperature that is at least 20° C. below the melting point of said thiophene, and said method (II) further comprises separating the precipitated solid thiophene from said cooled second solution at a temperature that is at least 20° C. below the melting point of said thiophene.

17. The process of claim 16, wherein said method (I) further comprises removing residual solvent from the precipitated solid thiophene by means of distillation, and said method (II) further comprises removing residual solvent from the precipitated solid thiophene by means of distillation.

18. The process of claim 10, wherein the said first solution and said second solution are each cooled to a temperature that is at least 20° C. below the melting point of said thiophene.

* * * * *